United States Patent [19]

Scherrer

[11] 4,452,979
[45] Jun. 5, 1984

[54] PROCESS FOR MAKING ENAMINES

[75] Inventor: Robert A. Scherrer, White Bear Lake, Minn.

[73] Assignee: Riker Laboratories, Inc., St. Paul, Minn.

[21] Appl. No.: 439,636

[22] Filed: Nov. 5, 1982

[51] Int. Cl.³ .......................................... C07D 333/20
[52] U.S. Cl. .................................. 544/58.7; 544/146;
544/379; 546/213; 548/336; 548/374; 548/527;
549/79
[58] Field of Search .................. 544/58.7, 146, 379;
546/213; 548/336, 374, 527; 549/78

[56] References Cited

U.S. PATENT DOCUMENTS 4,128,664 12/1978 Moore ................................. 424/324
4,172,082 10/1979 Moore ................................... 549/72

*Primary Examiner*—Richard Raymond
*Attorney, Agent, or Firm*—Donald M. Sell; James A. Smith; Robert W. Sprague

[57] ABSTRACT

A process for preparing antiinflammatory enamines of the following formula

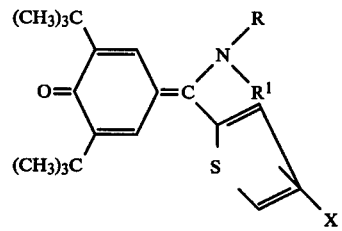

wherein R is lower alkyl; $R^1$ is selected from the group consisting of lower alkyl, benzyl, and N,N-dimethylaminoethyl; or R and $R^1$ are fused to form an optionally-substituted five- or six-membered heterocyclic ring; and X is hydrogen, methyl or halogen, comprising (a) reacting a 3,5-bis(t-butyl)-4- hydroxybenzoyl-substituted thiophene with a chlorine source selected from thionyl chloride and phosphorus pentachloride; and (b) reacting the resulting intermediate with an amine to provide the enamine.

11 Claims, No Drawings

PROCESS FOR MAKING ENAMINES

TECHNICAL FIELD

This invention relates to a novel synthetic process for the preparation of enamines which are antiflammatory agents. More specifically, it relates to an improved synthetic process for preparing enamines which include a thiophene ring, a bis(tertiary-butyl)quinone group and an amine group all bonded to a central olefinic carbon atom.

BACKGROUND OF THE INVENTION

U.S. Pat. No. 4,172,082 describes 3,5-bis(t-butyl)-4-hydroxybenzoyl-substituted thiophenes which exhibit antiinflammatory activity and are useful as starting materials in the process of the invention.

Enamines which are prepared by the process of the invention are disclosed in copending application Ser. No. 439,613. The processes claimed in that application involve an initial step in which the 3,5-bis(t-butyl)-4-hydroxybenzoyl-substituted thiophene is reacted with a strong base to provide a metal salt.

DETAILED DESCRIPTION OF THE INVENTION

This invention relates to a synthetic process for preparing enamines which are active antiinflammatory agents.

Specifically, this invention relates to a process for preparing an enamine of the formula

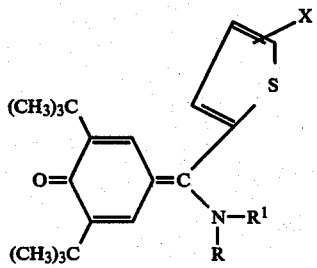

I wherein R is lower alkyl; $R^1$ is selected from the group consisting of lower alkyl, benzyl, and 2-(N,N-dimethylamino) ethyl; or R and $R^1$ are fused to form an optionally-substituted five- or six-membered heterocyclic ring; and X is hydrogen, methyl or halogen. The process of the invention comprises the steps of:

(1) reacting a compound of the formula

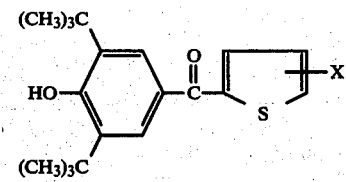

wherein X is as defined above, with a chlorine source selected from thionyl chloride and phosphorus pentachloride to provide an intermediate of the formula

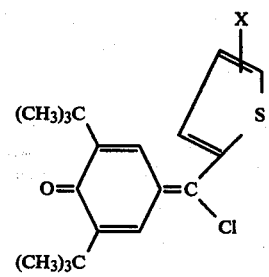

wherein X is as defined above; and
(2) reacting the intermediate from step 1 with an amine of the formula

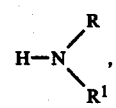

wherein R and $R^1$ are as defined above, to provide the enamine.

Thus it is seen that the process of the invention is an improvement in terms of convenience over the processes claimed in said copending application Ser. No. 439,613 in that the instant process eliminates the initial step in which the metal salt of 3,5-bis(t-butyl)-4-hydroxybenzoyl-substituted thiophene is formed.

"Lower alkyl" as used herein refers to an alkyl group containing one to six carbon atoms in straight or branched-chain configuration. Preferred lower alkyl groups contain one to four carbon atoms, and most preferred lower alkyl groups contain one or two carbon atoms.

Presently preferred compounds of Formula I which may be prepared using the process of the invention are those wherein X is hydrogen. Also, presently preferred compounds are those wherein $R^1$ is lower alkyl, benzyl or together with R forms a five or six-membered heterocyclic ring.

Heterocyclic rings formed by R and $R^1$ may be fully saturated or may be unsaturated. Examples of fully saturated rings (which include the N atom of Formula I) are pyrrolidinyl, piperidinyl, piperazinyl, prolyl

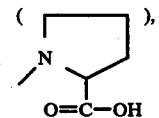

morpholinyl, N-lower alkylpiperazinyl, thiomorpholinyl and the like. Examples of unsaturated rings are pyrrolyl, imidazolyl, pyrazolyl and the like. It is presently preferred that the heterocyclic ring be fully saturated. The most preferred rings are pyrrolidinyl and piperidinyl.

The heterocyclic ring formed by R and $R_1$ is optionally substituted, and the substitutent is preferably lower alkyl and most preferably methyl.

Presently preferred compounds which may be prepared using the process of the invention are:
2,6-di-tert-butyl-4-[alpha-(1-piperidino)-alpha-(2-thienyl)]-methylidene-2,5-cyclohexadien-1-one
2,6-di-tert-butyl-4-[alpha-(N,N-dimethylamino)-alpha-(2-thienyl)]methylidene-2,5-cyclohexadien-1-one 2,6-di-tert-butyl-4-[alpha-(N,N-diethylamino)-alpha-(2-thienyl)]methylidene-2,5-cyclohexadien-1-one 4-[alpha-(N-benzyl-N-methylamino)-alpha-(2-thienyl)]-methylidene-2,6-di-tert-butyl-2,5-cyclohexadien-1-one 2,6-di-tert-butyl-4-[alpha-(1-pyrrolidinyl)-alpha-(2-thienyl)]methylidene-2,5-cyclohexadien-1-one The process of the invention is illustrated in the following Reaction Scheme:

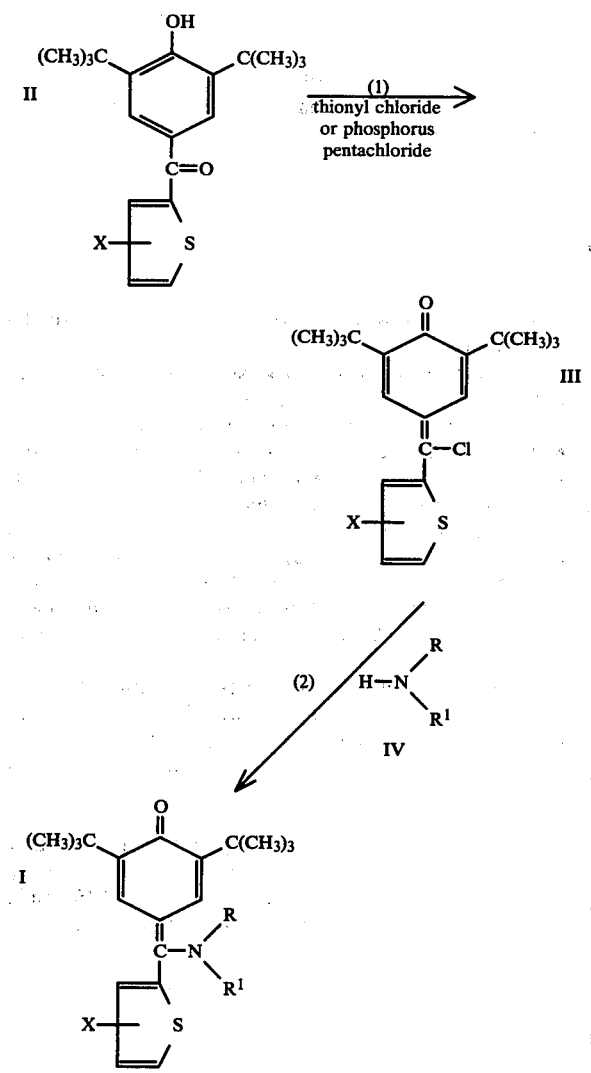

wherein R, R¹ and X are as defined previously.

In Step (1) the ketone or Formula II is reacted with thionyl chloride or phosphorus pentachloride to provide the intermediate of Fromula III. When the chlorinating agent is phosphorus pentachloride, the reaction is preferably conducted in an inert solvent such as benzene or toluene. When the chlorinating agent is thionyl chloride, it is preferred that no solvent be employed and it is also preferred that a small amount (e.g., generally less than 1% by volume is sufficient) of N,N-dimethylformamide be used as a catalyst. When the solvent is used with thionyl chloride it should be an inert organic solvent such as benzene, toluene, chloroform and the like. The reaction temperature will generally be between about 20° C. and the reflux temperature of the mixture. Care must be used to avoid hydrolysis of the intermediate of Formula III since hydrogen chloride by-product may catalyze hydrolysis of that intermediate in the presence of water.

In Step (2) the intermediate of Formula III is reacted with preferably about an equimolar amount of an amine of Formula IV to provide the compound of Formula I. The reaction is carried out by first dissolving the intermediate of Formula III in an inert solvent such as diethyl ether or (preferably) tetrahydrofuran and then adding an amine of Formula IV. Depending on the amine employed, it may be necessary to heat the reaction mixture at its reflux temperature to obtain a satisfactory reaction rate. Pyrrolidine reacts readily at a temperature of 20° C. and heating is therefore generally not required. The reaction of step (2) may be monitored chromatographically. The compound of Formula I is readily isolated as a solid by conventional methods.

In the case of weakly basic amines such as pyrrole and imidazole, the amine employed in step (2) may be in the form of an alkali metal salt.

Said copending application Ser. No. 439,613, incorporated herein by reference, describes pharmaceutical compositions containing the enamines which may be prepared by the process of the invention and pharmacological methods of using such enamines.

The process of the invention is illustrated in the following non-limiting examples.

EXAMPLE 1

Step (1)

A mixture of 5.0 g (0.0158 mole) of 2,6-di(tert-butyl)-4-(2'-thenoyl)phenol and 25 ml of thionyl chloride containing 2 drops of N,N-dimethylformamide was heated to a gentle reflux. Gas evolution was observed which continued for 1.5 hours. After gas evolution stopped, the mixture was evaporated to provide an oil. Benzene was added and the mixture was evaporated again to provide 6.6 g of 4-[alpha-chloro-alpha-(2-thienyl)]methylidene-2,6-di(tert-butyl)-2,5-cyclohexadien-1-one as a red oil. The identity of the product was verified by infrared spectral analysis and comparison with the purified material for which a satisfactory elemental analysis had been obtained. Pure product was obtained by chromatography through silica gel using carbon tetrachloride as the eluent.

Step (2)

To a solution of 6.0 g (17.9 mmole) of 4-[alpha-chloro-alpha-(2-thienyl)]methylidene-2,6-di(tert-butyl)-2,5-cyclohexadien-1-one (from Step (1)) in 100 ml of tetrahydrofuran was added a molar excess of piperidine. The mixture was heated on a steam bath for one hour, cooled and poured into water. The aqueous mixture was extracted with dichloromethane. The extracts were dried over magnesium sulfate, filtered and evaporated to provide a red residue. Trituration of the residue with hexane provided a red solid. The solid was recrystallized from a chloroform-hexane mixture to provide red crystals of 2,6-di(tert-butyl)-4-[alpha-(1-piperidino)-alpha-(2-thienyl)]methylidene-2,5-cyclohexadien-1-one, m.p. 173°–175° C. Analysis: Calculated for $C_{24}H_{33}NOS$: %C, 75.1; %H, 8.7; %N, 3.7. Found: %C, 75.3; %H, 9.0; %N, 3.4. The structural assignment was confirmed by infrared and nuclear magnetic resonance spectral analyses.

EXAMPLE 2

To a solution of 6.0 g (17.9 mmole) of 4-[alpha-chloro-alpha-(2-thienyl)]methylidene-2,6-di(tert-butyl)-2,5-cyclohexadien-1-one (from Example 1, Step (1)) in 100 ml of tetrahydrofuran was added a molar excess of the sodium salt of imidazole (prepared from sodium hydride and imidazole in boiling tetrahydrofuran). The solution was boiled for one hour, cooled and poured into water. The aqueous mixture was extracted with dichloromethane and the extracts were dried over magnesium sulfate and filtered. Evaporation of the filtrate provided a solid residue. The residue was recrystallized from a chloroform-hexane mixture to provide 2,6-di(-tert-butyl)-4-[alpha-(1-imidazolyl)-alpha-(2-thienyl)-]methylidene-2,5-cyclohexadien-1-one as an orange-colored solid, m.p. 171°–173° C. Analysis: Calculated for $C_{22}H_{25}N_2OS$: %C, 72.3; %H, 6.9; %N, 7.7. Found: %C, 72.3, %H, 7.4; %N, 7.3. The structural assignment was confirmed by infrared and nuclear magnetic resonance spectral analysis.

EXAMPLE 3

A mixture of 5.0 g (0.0158 mole) of 2,6-di(tert-butyl-(4-(2'-thenoyl)phenol and 3.5 g (0.17 mole) of phosphorus pentachloride in 25 ml of benzene was heated gently for 15 minutes and then heated at its reflux temperature for one hour until evolution of gas stopped. The mixture was then diluted with hexane and poured over ice. The organic phase was washed four times with cold water and once with saturated sodium chloride solution and was then dried over anhydrous sodium sulfate. The resulting organic solution containing 4-[alpha-chloro-alpha-(2-thienyl]methylidene-2,6-di(tert-butyl)-2,5-cyclohexadiene-1-one may be used directly for further reaction. The crude product obtained by evaporating the solvent was not stable. Stable product was obtained by chromatography over silica gel using carbon tetrachloride as the eluent.

EXAMPLES 4–12

Using the method of Example 1, Step (2), the amines indicated as starting materials in the following table may be reacted with 4-[alpha-chloro-alpha-(2-thienyl)-]methylidene-2,6-di(tert-butyl)-2,5-cyclohexadien-1-one (from Example 1, Step (1)) to provide the following compounds.

| Ex. No. | Amine Starting Material | Product of Formula I |
|---|---|---|
| 4 | dimethylamine | 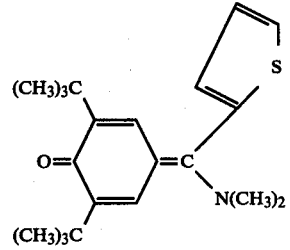 |
| 5 | diethylamine | 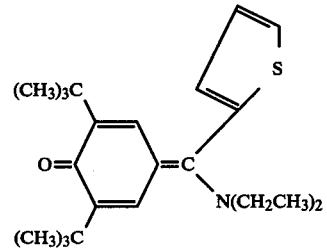 |
| 6 | triethylamine salt of proline | 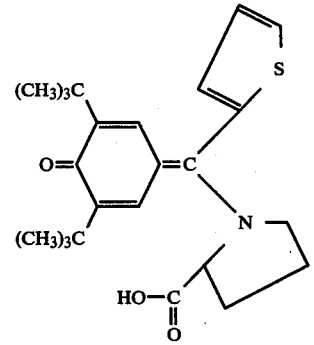 |

-continued
| Ex. No. | Amine Starting Material | Product of Formula I |
|---|---|---|
| 7 | N—methylpiperazine | 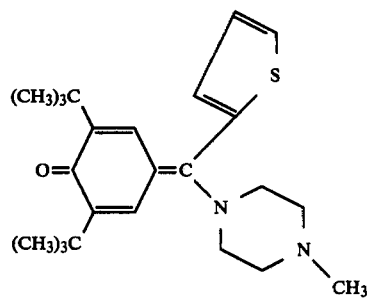 |
| 8 | N—(n-butyl)piperazine | 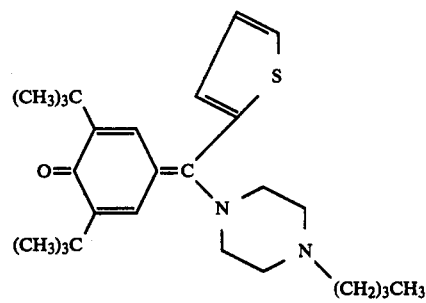 |
| 9 | thiomorpholine | 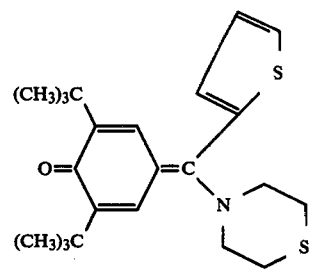 |
| 10 | pyrrole | 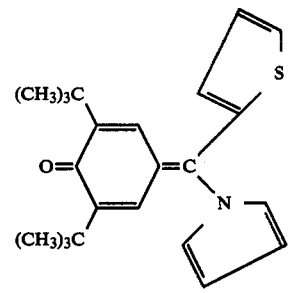 |
| 11 | pyrazole | 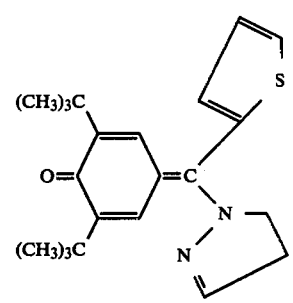 |

| Ex. No. | Amine Starting Material | Product of Formula I |
|---|---|---|
| 12 | morpholine | 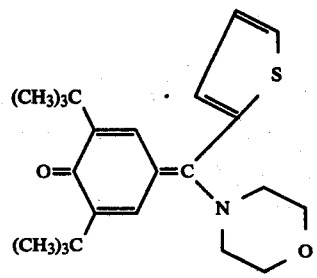 |

EXAMPLES 13–17

Using the method of Example 1, Steps (1) and (2), the following compounds of Formula I may be prepared from the indicated starting material of Formula II and the indicated amine of Formula IV:

| Ex. No. | Starting Material of Formula II | Amine of Formula IV | Compound of Formula I |
|---|---|---|---|
| 13 | | piperidine | |
| 14 | | pyrrolidine | |
| 15 | | diethylamine | |

| Ex. No. | Starting Material of Formula II | Amine of Formula IV | Compound of Formula I |
|---|---|---|---|
| 16 | 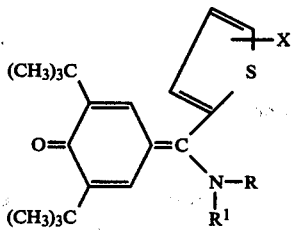 | pyrrolidine | |
| 17 | 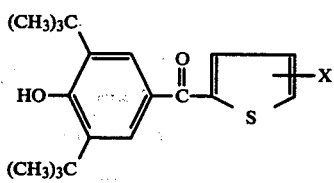 | pyrrolidine | |

What is claimed is:

1. A process for the preparation of an enamine of the formula wherein R is lower alkyl; R¹ is selected from the group consisting of lower alkyl, benzyl, and 2-(N,N-dimethylamino)ethyl; or R and R¹ are fused to form an optionally-substituted five- or six-membered heterocyclic ring, and X is hydrogen, methyl or halogen, comprising the steps of (1) reacting a compound of the formula wherein X is as defined above, with a chlorine source selected from thionyl chloride and phosphorus pentachloride to provide an intermediate of the formula

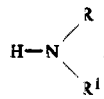

wherein X is as defined above, and (2) reacting the intermediate from step (1) with an amine of the formula $$H-N\begin{matrix}R\\R^1\end{matrix}$$

wherein R and R¹ are as defined above, to provide said enamine.

2. A process in accordance with claim 1, wherein said chlorine source is thionyl chloride.

3. A process in accordance with claim 2, wherein step (1) is conducted in the presence of a small amount of N,N-dimethylformamide as a catalyst.

4. A process in accordance with claim 2, wherein step (1) is conducted in the absence of a solvent.

5. A process in accordance with claim 1, wherein said chlorine source is phosphorus pentachloride.

6. A process in accordance with claim 1, wherein R is lower alkyl.

7. A process in accordance with claim 1, wherein R and R¹ are lower alkyl.

8. A process in accordance with claim 1, wherein R is methyl or ethyl and R¹ is methyl, ethyl or benzyl.

9. A process in accordance with claim 1, wherein R and R¹ are fused to form a five- or six-membered heterocyclic ring.

10. A process in accordance with claim 9, wherein said heterocyclic ring is selected from the group consisting of pyrrolidinyl, piperidinyl, piperazinyl, N-lower alkyl piperazinyl, prolyl, morpholinyl, thiomorpholinyl, pyrrolyl, imidazolyl, and pyrazolyl.

11. A process in accordance with claim 9, wherein said heterocyclic ring is selected from the group consisting of pyrrolidinyl and piperidinyl.

* * * * *